United States Patent [19]
Bleul et al.

[11] Patent Number: 5,753,233
[45] Date of Patent: May 19, 1998

[54] SEROREACTIVE EPITOPES ON PROTEINS OF HUMAN PAPILLOMA-VIRUS (HPV) 18

[75] Inventors: Conrad Bleul, Heidelberg; Lutz Gissmann, Wiesloch; Martin Müller, Heidelberg, all of Germany

[73] Assignee: Behring Diagnostics GmbH, Marburg, Germany

[21] Appl. No.: 466,285

[22] Filed: Jun. 6, 1995

Related U.S. Application Data

[62] Division of Ser. No. 164,768, Dec. 10, 1993, which is a continuation of Ser. No. 947,992, Sep. 21, 1992, abandoned, which is a continuation of Ser. No. 696,953, May 8, 1991, abandoned.

[30] Foreign Application Priority Data

May 10, 1990 [DE] Germany ............ 40 15 044.5

[51] Int. Cl.$^6$ .............. A61K 39/12; A61K 39/00; C12Q 1/70; G01N 33/53
[52] U.S. Cl. .............. 424/204.1; 424/184.1; 435/5; 435/7.1
[58] Field of Search .............. 424/204.1, 184.1; 435/5, 7.1

[56] References Cited

U.S. PATENT DOCUMENTS 4,777,239  10/1988  Schoolnik et al. .............. 530/326

FOREIGN PATENT DOCUMENTS 0 257 754  3/1988  European Pat. Off. .

OTHER PUBLICATIONS

Seedorf, K. et al., "Human Papillomavirus Type 16 DNA Sequence," Virology 145:181–185 (1985).

Seedorf et al., "Identification of early proteins of the human papilloma viruses type 16 (HPV 16) and type 18 (HPV 18) in cervical carcinoma cells," The EMBO Journal, vol. 6, No. 1, pp. 139–144 (1987).

Selvey, L.A., et al., "Identification of B–Epitopes in the Human Papillomavirus 18 E7 Open Reading Frame Protein," The Journal of Immunology, vol. 145, No. 9, pp. 3105–3110 (1990).

Smith, G. P., "Filamentous Fusion Phage: Novel Expression Vectors That Display Cloned Antigens on the Virion Surface," Science 228:1315–1317 (1985).

Wood, E.B., "Host Specificity of DNA produced by *Escherichia coli*: Bacterial Mutations affecting the Restriction and Modification of DNA," J. Mol. Biol. 16:118–133 (1966).

Hanahan, D., "Studies on Transformation of *Escherichia coli* with Plasmids," J. Mol. Biol. 166:557–580 (1983).

Lyons, L.B. et al., "The Genetic Map of the Filamentous Bacteriophage f1," Virology 49:45–60 (1972).

Matlashewski, G. et al., "The expression of human papillomavirus type 18 E6 protein in bacteria and the production of anti–E6 antibodies," Chem. Abstracts 106:1115k (1987).

Matlashewski, G. et al., The Expression of Human Papillomavirus Type 18 E6 Protein in Bacteria and the Production of Anti–E6 Antibodies, J. Gen. Virol. 67:1909–1916 (1986).

Parmley, S.F. et al., "Antibody–selectable filamentous fd phage vectors: affinity purification of target genes," Gene 73:305–318 (1988).

Sanger, F. et al., "DNA sequencing with chain–terminating inhibitors," Proc. Natl. Acad. Sci. USA, vol. 74:5463–5467 (1977).

Bleul, C. et al., "Human Papillomavirus Type 18 E6 and E7 Antibodies in Human Sera: Increased Anti–E7 Prevalence in Cervical Cancer in Patients," Journal of Clinical Microbiology, vol. 29, 1579–1588 (1991).

Cole, S.T. et al., "Nucleotide sequence and comparative analysis of the human papillomavirus type 18 genome. Phylogeny of papillomaviruses and repeated structure of E6 and E7 gene products," Chem. Abstracts 107:53075n (1987).

Durst, M. et al., "A papillomavirus DNA from a cervical carcinoma and its prevalence in cancer biopsy samples from different geographic regions," Proc. Natl. Acad. Sci., USA, vol. 80, pp. 3812–3815 (1983).

Geysen, H.M. et al., "Small peptides induce antibodies with a sequence and structural requirement for binding antigen comparable to antibodies raised against the native protein," Proc. Natl. Acad. Sci. USA, vol. 82:178–182 (1985).

Geysen et al., "Use of peptide synthesis to probe viral antigens for epitopes to resolution of a single amino acid," Proc. Natl. Acad. Sci., USA, vol. 81:3998–4002, (1984).

*Primary Examiner*—Lynette F. Smith
*Attorney, Agent, or Firm*—Finnegan, Henderson, Farabow, Garrett & Dunner, L.L.P.

[57] ABSTRACT

The invention relates to seroreactive epitopes on proteins of human papillomavirus HPV18.

In addition, the invention relates to peptides which have amino-acid sequences which coincide in whole or in part with the sequences of the seroreactive epitopes, and to vaccines which contain such peptides.

10 Claims, No Drawings

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Thr  Glu  Asn  Ser  Pro  Leu  Gly  Glu  Arg  Leu  Glu  Val  Asp  Thr  Glu  Leu
 1                  5                        10                       15

Ser  Pro  Arg  Leu  Gln  Glu  Ile  Ser  Leu  Asn  Ser
                20                       25
```

( 2 ) INFORMATION FOR SEQ ID NO:2:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp  Pro  Thr  Arg  Arg  Pro  Tyr  Lys  Leu  Pro  Asp  Leu  Cys  Thr  Glu  Leu
 1                  5                        10                       15

Asn  Thr  Ser  Leu  Gln  Asp  Ile  Glu  Ile  Thr  Cys  Val  Tyr  Cys  Lys  Thr
                20                       25                       30
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met  Ala  Arg  Phe  Glu  Asp  Pro  Thr  Arg  Arg  Pro  Tyr  Lys  Leu
 1                  5                        10
```

(2) INFORMATION FOR SEQ ID NO:4:

(i) SEQUENCE CHARACTERISTICS:
(A) LENGTH: 32 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

Ala Ala Cys His Lys Cys Ile Asp Phe Tyr Ser Arg Ile Arg Glu Leu
1               5                   10                  15
Arg His Tyr Ser Asp Ser Val Tyr Gly Asp Thr Leu Glu Lys Leu Thr
            20                  25                  30

(2) INFORMATION FOR SEQ ID NO:5:

(i) SEQUENCE CHARACTERISTICS:
(A) LENGTH: 48 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

Val Leu His Leu Glu Pro Gln Asn Glu Ile Pro Val Asp Leu Leu Cys
1               5                   10                  15
His Glu Gln Leu Ser Asp Ser Glu Glu Glu Asn Asp Glu Ile Asp Gly
            20                  25                  30
Val Asn His Gln His Leu Pro Ala Arg Arg Ala Glu Pro Gln Arg His
            35                  40                  45

(2) INFORMATION FOR SEQ ID NO:6:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

Ile Asp Gly Val Asn His Gln His Leu Pro Ala Arg Arg
1               5                   10

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

TCCAGACGTT AGTAAATGAA                    20

SEROREACTIVE EPITOPES ON PROTEINS OF HUMAN PAPILLOMA-VIRUS (HPV) 18

This is a division of application Ser. No. 08/164,768, filed Dec. 10, 1993 which is a continuation application of Ser. No. 07/947,992, filed Sep. 21, 1992, abandoned, which was a continuation of Ser. No. 07/696,953, filed May 8, 1991, abandoned.

The invention relates to seroreactive regions on proteins E1, E6 and E7 of human papillomavirus (HPV) 18.

The invention also relates to vaccines which contain peptides which embrace amino-acid sequences of the seroreactive regions of the said virus proteins and to diagnostic kits which contain the said peptides.

HPV18 is a specific type of human papillomavirus which was described for the first time in Proc. Natl. Acad. Sci., USA 80, 3813–3815 (1983).

The DNA sequence and the organization of the viral genome of HPV18 were published in Virology 145, 181–185 (1985).

HPV18 induces not only benign lesions of the anogenital tract but also malignant tumors of the neck of the uterus, of the penis and of the vagina. However, HPV18 is also found in genital scrapings from clinically symptom-free individuals. To date little is known about the immune response to infection by HPV18 and other papillomaviruses.

In initial experiments, human sera from STD patients, from patients suffering from cervical tumors and from healthy individuals were tested for the presence of antibodies directed against viral proteins. These viral proteins were expressed as fusion proteins covalently bonded to various procaryotic peptides via their N terminus. Fusion proteins of this type were then used as antigens in Western blot experiments. However, this test is relatively time-consuming and complicated and can be carried out only with great expense, so that it appears unsuitable for quantitative analysis of large quantities of human serum. In addition, this test is not very specific because the various papillomavirus types are also related in respect of their protein core, and thus a cross-reaction of antibodies with proteins or fusion proteins from different papillomavirus types cannot be ruled out.

The object of the present invention is therefore to identify viral structures of HPV18 which are suitable as aids in the prophylaxis, the diagnosis and the therapy of HPV18-induced diseases in humans. Knowledge about such structures (protein domains) is a prerequisite for the establishment of a test with which large quantities of human blood serum can be examined for the presence of specific HPVs.

Thus the present invention embraces a seroreactive epitope on the E1 protein of HPV18 with the following amino-acid sequence

TENSPLGERLEVDTELSPRLQEISLNS (SEQ. ID NO:1)

and seroreactive epitopes on the E6 protein of HPV18 with one of the following amino-acid sequences

I. DPTRRPYKLPDLCTELNTSLQDIEITCVYCKT (SEQ. ID NO:2)

II. MARFEDPTRRPYKL (SEQ. ID NO:3)

III. AACHKCIDFYSRIRELRHYSDSVYGDTLEKLT (SEQ. ID NO:4) and seroreactive epitopes on the E7 protein of HPV18 with one of the following amino-acid sequences I. VLHLEPQNEIPVDLLCHEQLSDSEEEN-DEIDGVNHQHLPARRAEPQRH (SEQ. ID. NO:5) and

II. IDGVNHQHLPARR (SEQ. ID. NO:6).

The invention also embraces peptides which contain either one or more than one amino-acid sequence(s) according to the invention of the abovementioned seroreactive epitopes.

The invention also embraces vaccines which are based on peptides which contain one or more amino-acid sequence(s) of the abovementioned seroreactive epitopes of the proteins of HPV18.

Specific antibodies against HPV18 E1, E6 and E7 proteins can be detected in patients' sera using a diagnostic kit according to the invention. This kit contains the peptides according to the invention.

Moreover, it is also possible, with a view to prophylaxis, for the specific viral proteins which contain the seroreactive regions to be identified in blood serum in good time using polyclonal antibodies or monoclonal antibodies which are directed against these regions. Accordingly, this invention also embraces a diagnostic kit which contains polyclonal or monoclonal antibodies which are specifically directed against the seroreactive regions of HPV18.

The following mutually independent methods were used to identify the seroreactive epitopes:

A. Screening of a shotgun expression bank: the HPV18 DNA cloned in the bacterial plasmid vector pSP65 was converted into fragments with an average size of 100 base-pairs by ultrasonic shearing and subsequent DNase treatment. The ends of these fragments were filled in with T4 DNA polymerase and ligated into the phage expression vector fuse 1. Fuse 1 is derived from the bacteriophage fd and is described in Science 228, 1315–1317 (1985). The phages were plated out with *Escherichia coli* K91, replicas were made on nitrocellulose filters, and the filters were incubated with suitable polyclonal rabbit sera. Positive clones were isolated in several singling-out steps, and the immunoreactive peptide sequences were identified by DNA sequencing.

B. Peptide overlapping 127 overlapping peptides which correspond to short segments of the HPV18 E6 and E7 proteins were synthesized on polyethylene pins using Fmoc chemistry (Proc. Natl. Acad. Sci., 82, 178 (1985)). The protein sequence of the E6 and E7 proteins was divided into 10 mers which coincide in 8 amino acids with the next peptide. The peptides were assayed by ELISA in the appropriate antisera.

EXAMPLE 1

Derivatives of the filamentous phage fd were used to obtain an expression system for HPV18 DNA fragments. For this, fuse 1 (fd-tet-J6, Science 228, 1315–1317 (1985); Gene 73, 305–318 (1988)) was cut at the single PvuII cleavage site. Genomic HPV18 DNA fragments from a DNaseI digestion after DNA repair underwent blunt-end ligation with a T4 DNA ligase. To transform the fuse 1 vector, the *E. coli* strain K802 (F⁻ galK2 galT22 metBI supE44 hsdr(2); Journal of Molecular Biology 16, 118–133 (1966)) was used in the method of Hanahan in Journal of Molecular Biology 166, 557–580 (1988). The tet-resistant colonies produce bacteriophages which are not infectious for the bacteria because of their F⁻ phenotype. In order to plate out the phages, the *E. coli* strain K91 (F⁺, a derivative of *E. coli* K38, Virology 49, 45–60 (1972)) was used.

EXAMPLE 2

Approximately 50 000 recombinant phages from the random bank described above were plated out with 0.2 ml of exponentially growing *E. coli* K91 cells in 3.5 ml of 0.5% agarose, which contained 10 mM MgSO₄, on minimal agar plates. Replicas of the plates were made on nitrocellulose filters and then incubated further at 37° C. on fresh minimal agar for 6 h in order to enhance the signal. The filters were then blocked with 10% low-fat milk in PBS for 60 min and incubated in 5% milk/PBS with a dilution of HPV-specific antisera of from 1:100 to 1:1000 overnight. It is also possible to use monoclonal antibodies in place of the specific HPV antisera. The antisera were preadsorbed with sonicated K91 cells. The filters were then washed 5×, specifically in PBS/ 0.1% Tween 20 for 5 min and then at room temperature for 3 h with goat anti-rabbit antibodies or, in the case where monoclonal antibodies were used, incubated with anti-mouse peroxidase antibodies (1:1000) in 5% low-fat milk. After the filters had been washed they were stained in 50 ml of PBS which contained 30 mg of diaminobenzidine. 30 µl of 30% strength $H_2O_2$ and 1.5 ml of 1% strength $NiSO_4$. The filters were then washed in $H_2O$ for 30 min and then dried on filter paper.

Initially 25 phages were isolated using the polyclonal rabbit serum against HPV18 E7, and 18 of these proved positive in the subsequent purification steps. Subsequently, phage particles were grown in culture and single-stranded DNA was prepared.

EXAMPLE 3

The same approach as in Example 2 was also chosen for HPV18 E6 protein. Since the polyclonal rabbit serum used cross-reacted with non-viral epitopes, besides the Western blot method, specific DNA fragments were used as probes in order to identify among all the reactive recombinants those with HPV18 E6 portions. From 70 000 recombinant phages, 15 were isolated and finally sequenced. The epitope HPV18 E6 No. 1 was thus found a total of 10 times in the investigated phage bank, for example.

EXAMPLE 4

Preparation of single-stranded DNA from fuse 1 recombinants

Used for this was a procedure from Proc. Natl. Acad. Sci., USA 74, 5463–5467 (1977). 50 ml of LM were incubated with tet-resistant *E. coli* K91 cells which harbored the fuse 1 plasmid, and this mixture was incubated at 37° C. for 16 h. The bacteria were then pelleted at 6000 rpm for 30 min. After addition of 2 ml of 40% strength PEG 6000 and 2 ml of 5M sodium acetate, pH 6.5, to the supernatant, the phages were precipitated at 0° C. for 60 min, and the precipitate was centrifuged at 6000 rpm for 60 min. The pellet was resuspended in 0.3 ml of TE. Two phenol extractions were followed by precipitation of the DNA. Approximately 25% of the preparations were then used for the sequencing.

EXAMPLE 5

Sequencing

The standard USB (United States Biochemicals) method (USB, 1987) was used for the DNA sequencing. The universal primer was replaced by a 20 mer oligonucleotide (5'-TCCAGACGTTAGTAAATGAA-3 1') (SEQ. ID NO:7).

EXAMPLE 6

Peptide synthesis 127 overlapping peptides which represent in short segments the ORFs HPV18 E6 and E7 were synthesized by Fmoc chemistry on polyethylene pins as described in Proc. Natl. Acad. Sci. 82, 178 (1985) and Proc. Natl. Acad. Sci. 81, 3998 (1985). The polyethylene pins, which were derivatized with β-alanine, were obtained from CRB England. Deviating from the publications cited above, the protein sequence was divided into decapeptides which overlap by 8 amino acids with the adjacent peptide. The synthesis was carried out using Fmoc chemistry and in situ activation by BOP (Castro's reagent) (Tetrahedron Letters, 14, 1219 (1975)). Fmoc-amino acid derivatives (6 µmol), BOP and N-methylmorpholine solution were distributed in polyethylene pins (CRB) corresponding to the peptide sequence which is to be synthesized. All the other reactions were carried out in accordance with the CRB protocol.

EXAMPLE 7

The polyethylene pins were incubated by the ELISA assay method with the abovementioned polyclonal rabbit sera, and bound antibodies were detected using protein A-peroxidase. A background produced by non-specific binding was quantified by protein A incubation without the first antibody. The reactive peptides are located in regions which were identified by the phage screening as sero-reactive epitope.

All the assays were carried out on the peptides which were bonded covalently to the polyethylene pins and on which they had originally been synthesized. Racks with 96 pins which were fixed in such a configuration that they could be introduced into the wells of microtiter plates were used. The incubation for the ELISA was carried out while the pins were immersed in the wells. The pins were washed with methanol and PBS and then blocked with 0.25% gelatin. 0.1% Tween 20 in PBS at 37° C. for 2 h, followed by incubation at 37° C. for 1 h with sera which were diluted 1:200 to 1:4000 in 0.125% gelatin and 0.05% Tween 20. After another washing step with PBS/0.1% Tween 20, the pins were incubated with protein A-peroxidase 1:4000 at 37° C. for 1 h, followed by another washing step and staining with tetramethylbenzidine (TMB) for 15 min. The staining step was stopped by withdrawing the pins from the staining solution and adding 100 µl of a 0.2 molar $H_2SO_4$ solution. The absorption was then measured in an automatic ELISA reader. In order to remove the antibody-enzyme complex after the ELISA process, the pins were incubated with ultrasound (water bath, 30 W, 48 KHz) at 60° C. in PBS/1% SDS/0.1% β-mercaptoethanol for 1 h and were finally washed with methanol. The efficiency of this procedure was tested by means of an ELISA using protein A/peroxidase without involving a primary serum. The same peptides were assayed more than 40 times in the following ELISAS.

TABLE

E1 seroreactive epitope (HPV18)

| | |
|---|---|
| bp1193-TENSPLGERLEVDTELSPRLQEISLNS-bp1273 | (SEQ. ID NO: 1) |
| E6 seroreactive epitopes (HPV18) | |
| bp120-DPTRRPYKLPDLCTELNTSLQDIEITCVYCKT-bp215 | (SEQ. ID NO: 2) |
| MARFEDPTRRPYKL | (SEQ. ID NO: 3) |
| bp294-AACHKCIDFYSRIRELRHYSDSVYGDTLEKLT-bp386 | (SEQ. ID NO: 4) |
| E7 seroreactive epitope (HPV18) | |
| bp623-VLHLEPQNEIPVDLLCHEQLSDSEEENDEIDGVNHQHLPARRAEPQRH-bp763 | (SEQ. ID NO: 6) |
| IDGVNHQHLPARR | |

---

We claim:

1. The seroreactive epitope on the E1 protein of HPV 18 with the following amino acid sequence

TENSPLGERLEVDTELSPRLQEISLNS (SEQ. ID NO:1).

2. The seroreactive epitope on the E6 protein of HPV 18 with one of the following amino acid sequences I. DPTRRPYKLPDLCTELNTSLQDIEITCVYCKT (SEQ. ID NO:2),
II. MARFEDPTRRPYKL (SEQ. ID NO:3), and
III. AACHKCIDFYSRIRELRHYSDSVYGDTLEKLT (SEQ. ID NO:4).

3. The seroreactive epitope on the E7 protein of HPV 18 with one of the following amino acid sequences I. VLHLEPQNEIPVDLLCHEQLSDSEEEN-DEIDGVNH QHLPARRAEPQRH (SEQ. ID NO:5), and

II. IDGVNHQHLPARR (SEQ. ID NO:6).

4. A peptide excepting the entire E1 protein of HPV18 having the amino acid sequence claimed in claim 1.

5. A peptide, excepting the entire E6 protein of HPV 18, having at least one of the amino acid sequences selected from the group consisting of the amino acid sequences claimed in claim 2.

6. A peptide having at least one of the amino acid sequences selected from the group consisting of the amino acid sequences claimed in claim 3.

7. A diagnostic composition for identifying specific antibodies directed against protein E1 of HPV 18, comprising the peptide of claim 4.

8. A diagnostic composition for identifying specific antibodies directed against protein E6 of HPV 18, comprising the peptide of claim 5.

9. A diagnostic composition for identifying specific antibodies directed against protein E7 of HPV 18, comprising the peptide of claim 6.

10. A diagnostic composition for identifying viral proteins in patients' sera, comprising polyclonal or monoclonal antibodies with specificity for the seroreactive epitope of claim 1.

* * * * *